US012636468B2

(12) United States Patent
Beran et al.

(10) Patent No.: US 12,636,468 B2
(45) Date of Patent: May 26, 2026

(54) INTEGRATED TEMPERATURE SENSITIVE WOUND DRESSING DEVICE

(71) Applicants:Anthony V Beran, Irvine, CA (US);
Kerry J Tomic-Edgar, Irvine, CA (US)

(72) Inventors: Anthony V Beran, Irvine, CA (US);
Kerry J Tomic-Edgar, Irvine, CA (US)

( * ) Notice: Subject to any disclaimer, the term of this patent is extended or adjusted under 35 U.S.C. 154(b) by 917 days.

(21) Appl. No.: 17/843,832

(22) Filed: Jun. 17, 2022

(65) Prior Publication Data

US 2022/0323721 A1      Oct. 13, 2022

Related U.S. Application Data

(63) Continuation-in-part of application No. 15/932,501, filed on Mar. 7, 2018, now abandoned.

(51) Int. Cl.
*A61M 25/02* (2006.01)
(52) U.S. Cl.
CPC ..... *A61M 25/02* (2013.01); *A61M 2025/0273* (2013.01); *A61M 2205/0205* (2013.01); *A61M 2205/3368* (2013.01); *A61M 2205/584* (2013.01)
(58) Field of Classification Search
CPC .. A61M 2025/0273; A61M 2025/0266; A61M 2025/0293; A61M 25/01; A61M 25/02; A61M 25/0612; A61M 2205/0205; A61M 2205/3368; A61M 2205/584; A61F 2013/00182; A61F 2013/002; A61F 2013/00412; A61F 2013/00089; A61F 2013/00582; A61F 13/00051; A61F 13/00063; A61F 13/0259; A61F 13/00; G01K 13/20

USPC .................................... 602/41, 42, 54, 57.59
See application file for complete search history.

(56) References Cited

U.S. PATENT DOCUMENTS

| | | | | | |
|---|---|---|---|---|---|
| 3,661,142 | A | * | 5/1972 | Flam ...................... | A61B 5/015 |
| | | | | | 374/162 |
| 9,320,840 | B2 | * | 4/2016 | Angel ................... | A61M 1/741 |
| 2016/0367789 | A1 | * | 12/2016 | Beran ................... | A61M 25/02 |

FOREIGN PATENT DOCUMENTS

| | | | | | |
|---|---|---|---|---|---|
| AU | 2014226388 | A1 | * | 10/2015 | ....... A61F 13/00063 |
| CA | 2864281 | A1 | * | 8/2013 | ............ A61M 25/02 |

* cited by examiner

*Primary Examiner* — Caitlin A Carreiro
(74) *Attorney, Agent, or Firm* — Gray Law Firm; Gordon E. Gray, III

(57) ABSTRACT

An integrated wound dressing device for treatment of an insertion site of percutaneous and drug delivery devices has a transparent film layer with a bottom side, a top side and a perimeter. The bottom side is coated with an adhesive impregnated with an antimicrobial agent. The transparent film has a radius cutout between a central opening and the perimeter. A liquid crystal temperature sensitive film with an adhesive placed on the top side of the transparent film layer is preferably near and around the central opening. The dressing also has a layer of double folded release paper below the bottom side of the transparent film layer. The preferred TLCs used are cholesteryl esters with a preferable temperature detection range of 35-40° C. The preferred antimicrobial agent is chlorohexidine gluconate (CHG).

6 Claims, 20 Drawing Sheets

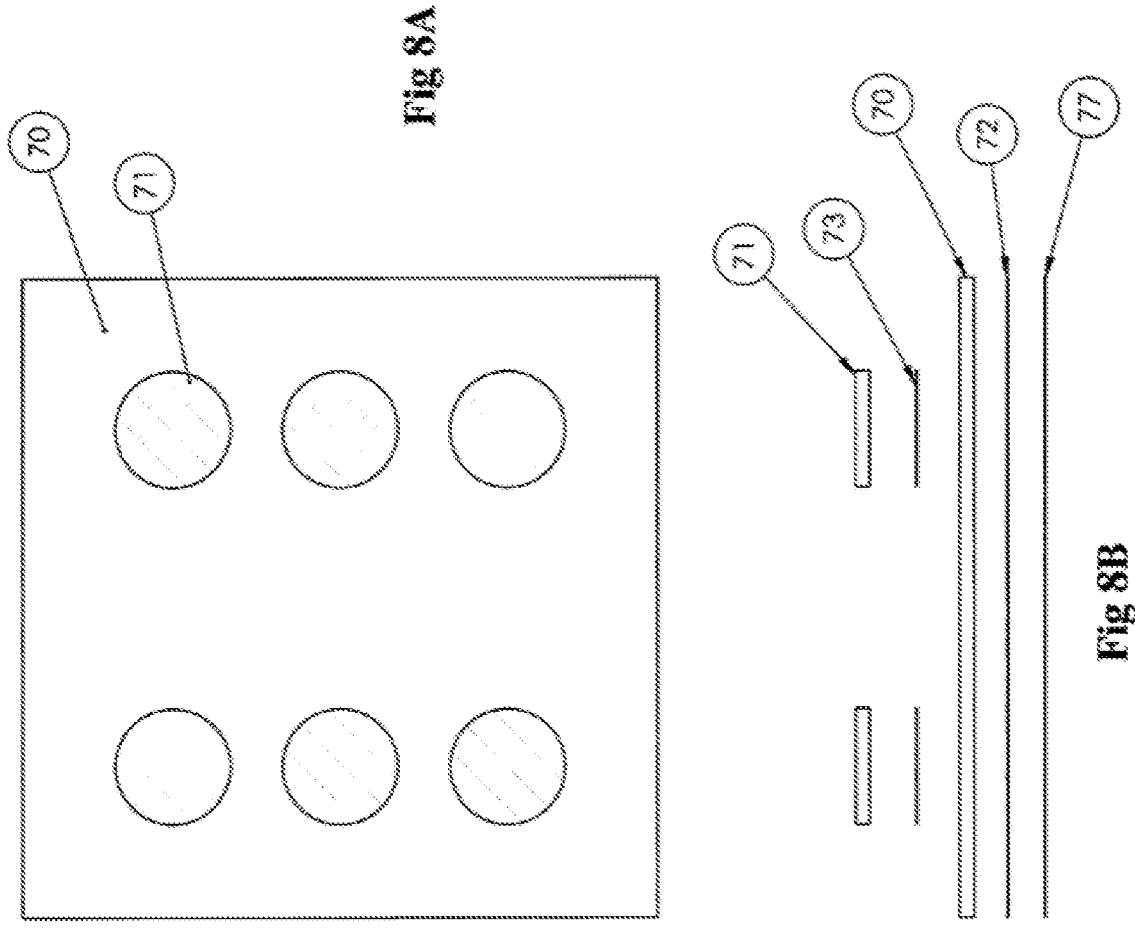

SECTION A-A

INTEGRATED TEMPERATURE SENSITIVE WOUND DRESSING DEVICE

This application is a continuation in part application of U.S. patent Ser. No. 15/932,501, which is incorporated herein by reference in its entirety.

TECHNICAL FIELD

The present invention pertains to an integrated wound dressing device for treatment of an insertion site of percutaneous and drug delivery devices.

BACKGROUND ART

Intravascular (IV) catheters are widely used in clinical situations. All patients with IV catheters risk developing complications related to catheter placement. Among the many complications reported, infection is the most problematic. When skin is compromised, such as during catheter insertion, it provides a path for bacteria to migrate along the catheter wall and cause an infection. This bacterial migration is further facilitated by catheter movement and micropistoning. The estimates of the occurrences of Central Line Blood Stream Infections (CLABSIs) in the United States is approximately 250,000 cases per year. These infections are associated with a high mortality rate (12-25%) and extended hospital stays of an additional 9-12 days. This can result in an increase of the cost of treatment by $34,000-$56,000 per patient.

Recently, a product that incorporates antimicrobial properties and is placed around the catheter insertion site, has been introduced in the clinical practice. The product is design to decrease bacterial flora on the skin surface around the catheter insertion site. The product comes in a form of circular patch made of synthetic and biopolymer composite foam/sponge impregnated with Chlorohexidine Gluconate (CHG). The product is referred to by its trademark, BIO-PATCH™. However, BIOPATCH™ is non-transparent and it does not have an adhesive on its lower/patient side. It is secured around the insertion site by secondary transparent film with adhesive. A transparent film dressing that permits a visual observation of catheter insertion site is disclosed in U.S. Pat. No. 5,372,589. The product utilizing this patent is sold under the trademark SorbaView SHIELD™, but it is for a transparent dressing alone. U.S. Pat. No. 5,833,665 discloses a non-transparent foam pad with an adhesive layer on the bottom/patient side. U.S. Pat. No. 8,969,649 discloses a transparent film with acrylic adhesive impregnated with CHG The use of these commercially available products has decreased the potential for infection, but it could be further decreased. One way to achieve a further decrease is to detect a local infection at its very beginning stage before it spreads systemically. The first sign of local infection is often local skin redness accompanied with elevated skin temperature around the insertion site. Thus, a device that aids in early detection of infections at catheter insertion sites is desired.

SUMMARY OF THE INVENTION

The present invention pertains to an integrated wound dressing device for treatment of an insertion site of percutaneous and drug delivery devices. The integrated wound dressing device preferably comprises a transparent film layer having a bottom side, a top side and a perimeter. The bottom side is coated with an adhesive impregnated with an antimicrobial agent. The transparent film has a radius cutout between a central opening and the perimeter. A liquid crystal temperature sensitive film with an adhesive placed on the top side of the transparent film layer is preferably near and around the central opening. The dressing also has a layer of double folded release paper below the bottom side of the transparent film layer. The preferred TLCs used are cholesteryl esters with a preferable temperature detection range of 35–40° C. The preferred antimicrobial agent is chlorohexidine gluconate (CHG).

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 8A is a top view of another embodiment of the invention;

FIG. 8B is a side view of the embodiment in FIG. 8A;

DETAILED DESCRIPTION OF THE PREFERRED EMBODIMENTS

Figures 1A, 1B:
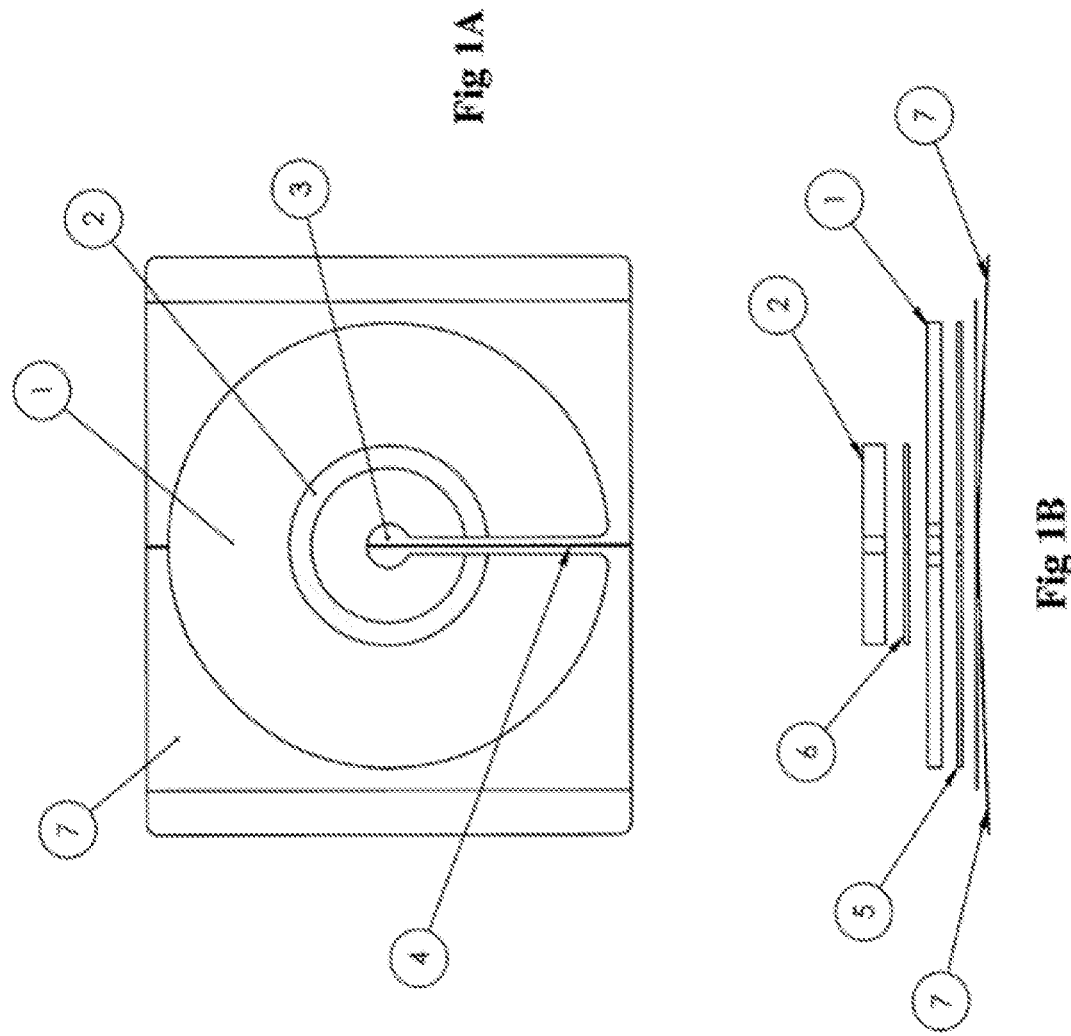
FIG. 1A is a top view of a preferred embodiment of the invention.
FIG. 1B is a side view of the embodiment in FIG. 1A.

Various embodiments are now described with reference to the drawings, wherein like reference numerals are used to refer to like elements throughout. In the following description, for purposes of explanation, numerous specific details are set forth in order to provide a thorough understanding of one or more embodiments. It may be evident, however, that such embodiment(s) may be practiced without these specific details.

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s). The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved integrated wound dressing device for treatment of an insertion site of percutaneous and drug delivery devices.

The invention preferably incorporates Temperature Sensitive Liquid Crystal (TLC) carrier with antimicrobial carrier, for early detection of local infection, by displaying changes in skin temperature around catheter insertion site. This integrated device preferably provides: a delivery of antibacterial agent around the catheter insertion site, a removal of exudate from around the insertion site, and a detection of changes in skin temperature around the insertion site.

Delivery of antimicrobial agents is preferably obtained by incorporating substances like CHG with sponge like materials, copolymers films or castings and adhesives. Some examples of other antimicrobial agents that can be used are: Chlorohexidine acetate, silver iodine, silver bromide, nanoparticulate metallic silver, benzo conium chloride, and triclosone.

Removal of exudate is preferably done by selecting a transparent film or casting that has the most adequate ratio of static fluid absorption and gas/vapor transmission.

Change in temperature is preferably observed by placing TLC film in different areas over the antimicrobial transparent film, or by mixing non-toxic mixtures of TLC with CHG within co-polymers or adhesives. The TLC, in order to function properly, is preferably protected from the environment. This protection can be achieved by:

A. TLC dispersion: TLC is dispersed as a discrete aggregate into the polyurethane materials such as polyurethane elastomers and polyurethane polymers. Films, sheets, castings or other three-dimensional forms of compounded mixtures, following proper polymerization, can be used as a temperature indicator. By properly selecting polyurethane for sponge formulation, the TLC can be incorporated into sponge structure. Or, B. TLC microencapsulation: TLC is treated by microencapsulation process to produce microencapsulated discrete globs of liquid crystal, each coated separately, which then can be incorporated into a carrier of selective functions.

The preferred urethane compounds for this invention are polyols, polyamines, polyamides or other suitable compounds. The preferred TLCs used are cholesteryl esters such as chloride, iodide, bromide, cinnamate, oleyl carbonate, acetate, nonanoate, hexanoate, linolineate, oleate, laurate, caproate, myristrate, hydrogen phthalate, benzoate, and others disclosed in U.S. Pat. No. 3,872,050. Different temperature ranges can be detected using different mixtures or rations of several TLC compounds in a single formulation or using a multilayer dispersion of several specific TLC. The temperature range is preferably 35-40 degrees Celsius (° C.).

To obtain better visibility of changes in colors, as a result in changes in temperature, the following can be performed: 1.) Polymerized temperature sensitive compound can be deposited on a dark background film; 2.) A carbonaceous black powder can be mixed during the TLC dispersion process; or, 3.) carbonaceous powder can be mixed during the microencapsulation process.

Referring now to FIG. 1A, a top view of the invention is shown. A gas and water vapor permeable transparent film 1 is shown. The bottom side of the film 1 is preferably coated with an acrylic adhesive impregnated with/permeated by an antimicrobial agent. A common example of such a film with antimicrobial adhesive is Bene Hold™ CHG transparent dressing. The bottom side is also referred to as the "patient side" because it contacts the patient's skin. The top side of the transparent film 1 is preferably smooth and faces away from the patient. Preferably, the transparent film 1 has a circular shape with an opening 3 placed in the center of the circle. As shown, a liquid crystal temperature sensitive film 2 with an adhesive, such as Edmund Optics™ liquid crystal sheet, having a 35-40° C. range, is placed centrally around the opening 3 on the top side of the transparent film 1. A radius cutout 4 preferably provides a passage between the center cutout 3 and the perimeter of the transparent film 1. The transparent film 1 is preferably placed over two pieces of double folded released paper 7 with two internal edges of a release paper folds, being aligned with the radius cutout 4, for easy placement of the invention around a catheter insertion site (not shown). In application, the radius cutout 4 is slid along the side of the catheter (not shown), until the catheter extends through the center cutout 3. The wings of double folded release paper 7 are then pulled off to expose the adhesive on the bottom side so that the invention can be secured to the skin of the patient.

Referring now to FIG. 1B, a side view of the embodiment shown in FIG. 1A is shown. As discussed above, the transparent film 1 is preferably covered with an antimicrobial adhesive 5 and placed over the two parts of a double folded release paper 7. The liquid crystal temperature sensitive film 2 with adhesive 6 on its bottom surface is placed on the top surface of the transparent film 1. The liquid crystal film 2, preferably in the form of a ring, is placed around center cut out 3. In this configuration, the changes in temperature are observed 360 degrees around a catheter insertion site and in proximity to the insertion site. Preferably, there is space between the inner circumference of the liquid crystal film 2 and the central opening 3 and, thus, the outer circumference of the catheter (not shown) for visual observation of the patient's insertion site.

Figures 2A, 2B:
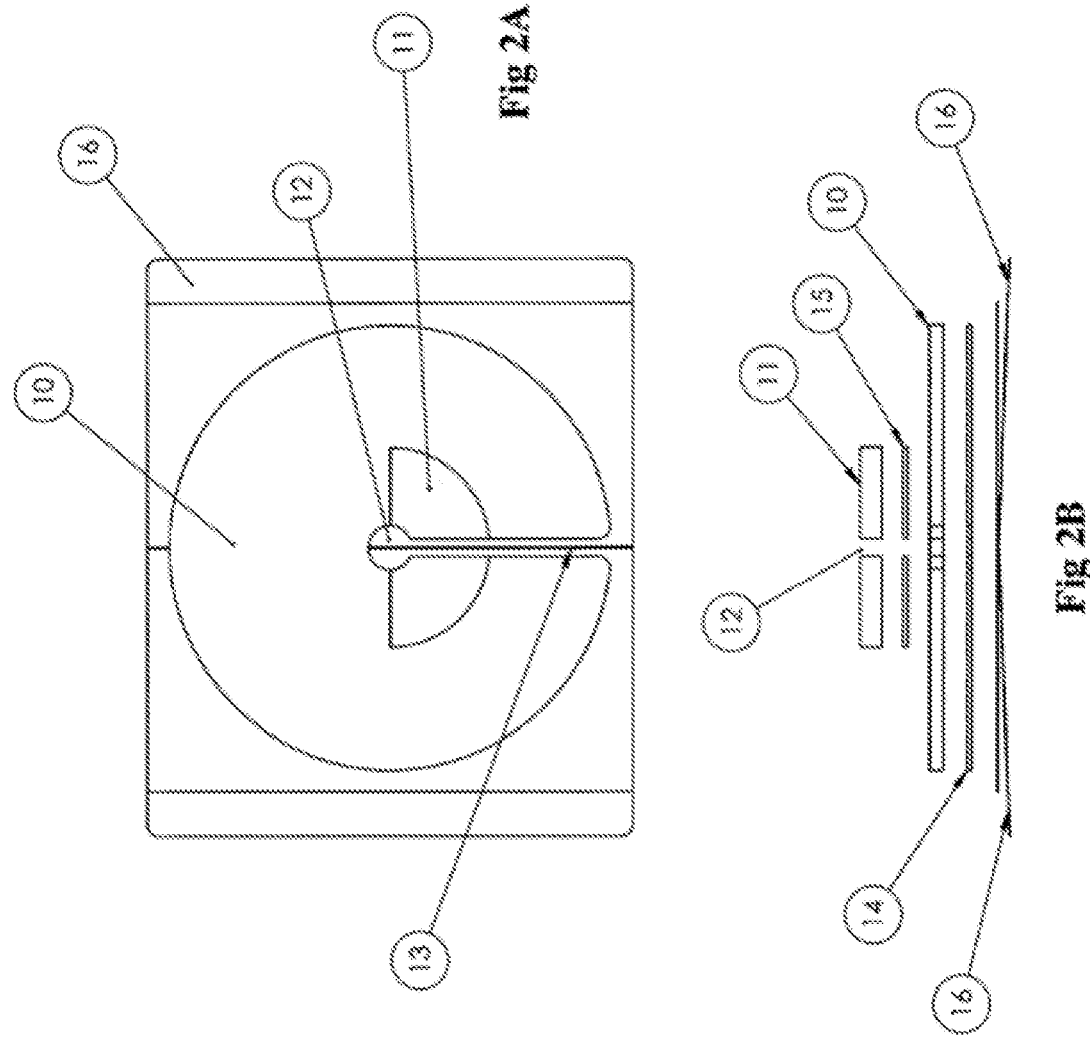
FIG. 2A is a top view of another embodiment of the invention.
FIG. 2B is a side view of the embodiment in FIG. 2A.

Referring now to FIG. 2A, a top view of another embodiment of the present invention is shown. A gas and water vapor permeable transparent film 10 is shown. The bottom side of the film 10 is preferably coated with an acrylic adhesive impregnated with/permeated by an antimicrobial agent. The top side of the transparent film 10 is preferably smooth and faces away from the patient. Preferably, the transparent film 10 has a circular shape with an opening 12 placed in the center of the circle. As shown, a liquid crystal temperature sensitive film 11 with an adhesive is placed centrally half way around the opening 12 on the top side of the transparent film 10. A radius cutout 13 preferably provides a passage between the center cutout 12 and the perimeter of the transparent film 10. The transparent film 10 is preferably placed over two pieces of double folded released paper 16 with two internal edges of a release paper folds, being aligned with the radius cutout 13, for easy placement of the invention around a catheter insertion site (not shown).

Referring now to FIG. 2B, a side view of the embodiment shown in FIG. 2A is shown. As discussed above, the transparent film 10 is preferably covered with an antimicrobial adhesive 14 and placed over the two parts of a double folded release paper 16. The liquid crystal temperature sensitive film 11 with adhesive 15 on its bottom surface is placed on the top surface of the transparent film 10. The liquid crystal film 11, preferably in the form of a half ring, is placed around center cut out 12. In this configuration, the changes in temperature are observed 180 degrees around a catheter insertion site and in proximity to the insertion site while the other 180 degrees provides for visible observation of the insertion site.

Figures 3A, 3B:
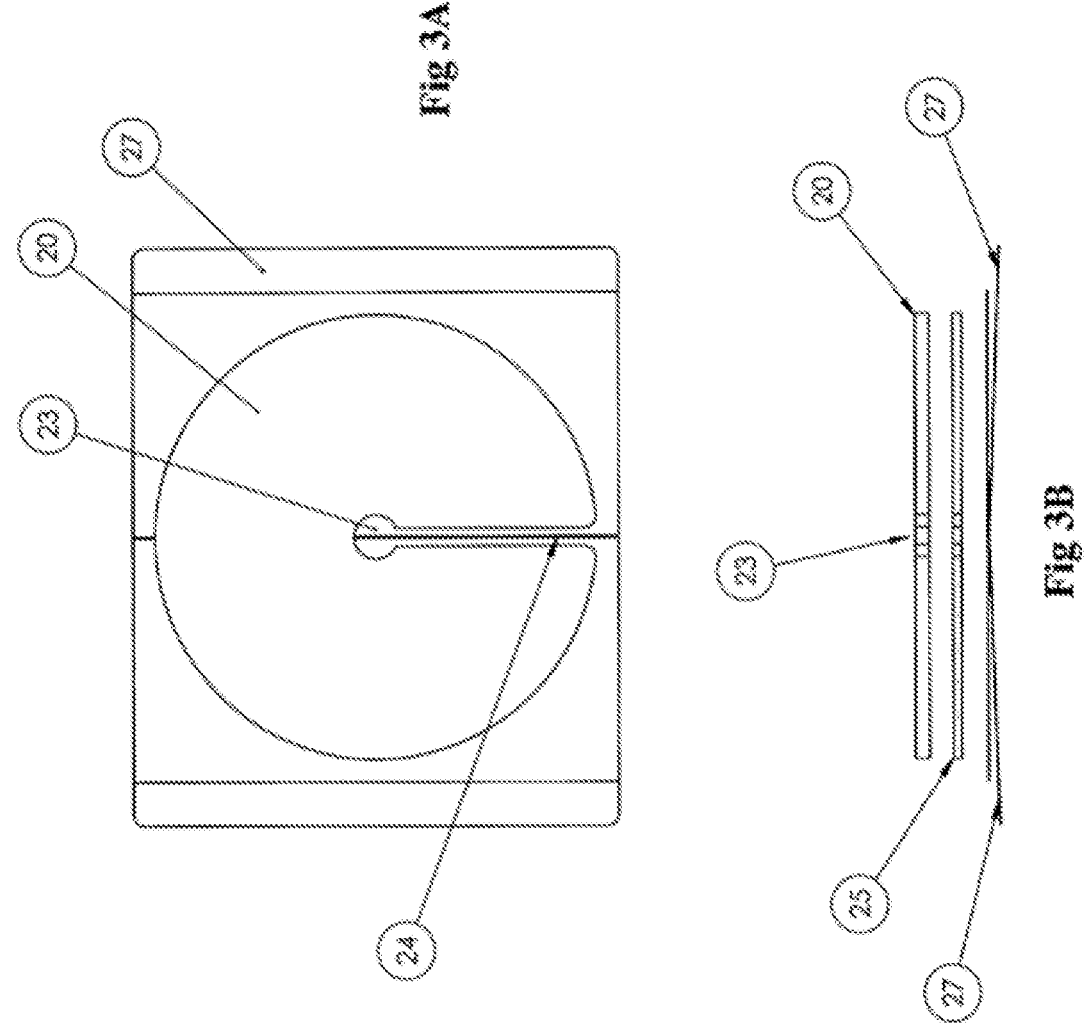
FIG. 3A is a top view of another embodiment of the invention.
FIG. 3B is a side view of the embodiment in FIG. 3A.

Referring now to FIG. 3A, a top view of another embodiment of the present invention is shown. In this embodiment, a transparent film 20 has its bottom surface covered with an acrylic adhesive impregnated or mixed with an antimicrobial agent and a non-toxic mixture of liquid crystal esters, providing for observation of temperature changes by observing the changes in color over the entire transparent film area. Preferably, the transparent film 20 has a circular shape with an opening 23 placed in the center of the circle. A radius cutout 24 preferably provides a passage between the center cutout 23 and the perimeter of the transparent film 20. The transparent film 20 is preferably placed over two pieces of double folded released paper 27 with two internal edges of a release paper folds, being aligned with the radius cutout 24, for easy placement of the invention around a catheter insertion site (not shown). A visual observation of the insertion site is limited with this embodiment because microencapsulated globes of TLC, which are dispersed through the acrylic adhesive, are preferably coated with the carrier mixed with black powder.

Referring now to FIG. 3B, a side view of the embodiment shown in FIG. 3A is shown. As discussed above, the transparent film 20 is preferably covered with an antimicrobial adhesive mixed with microencapsulated globs of TLC 25 and placed over the two parts of a double folded release paper 27.

Figures 4A, 4B:
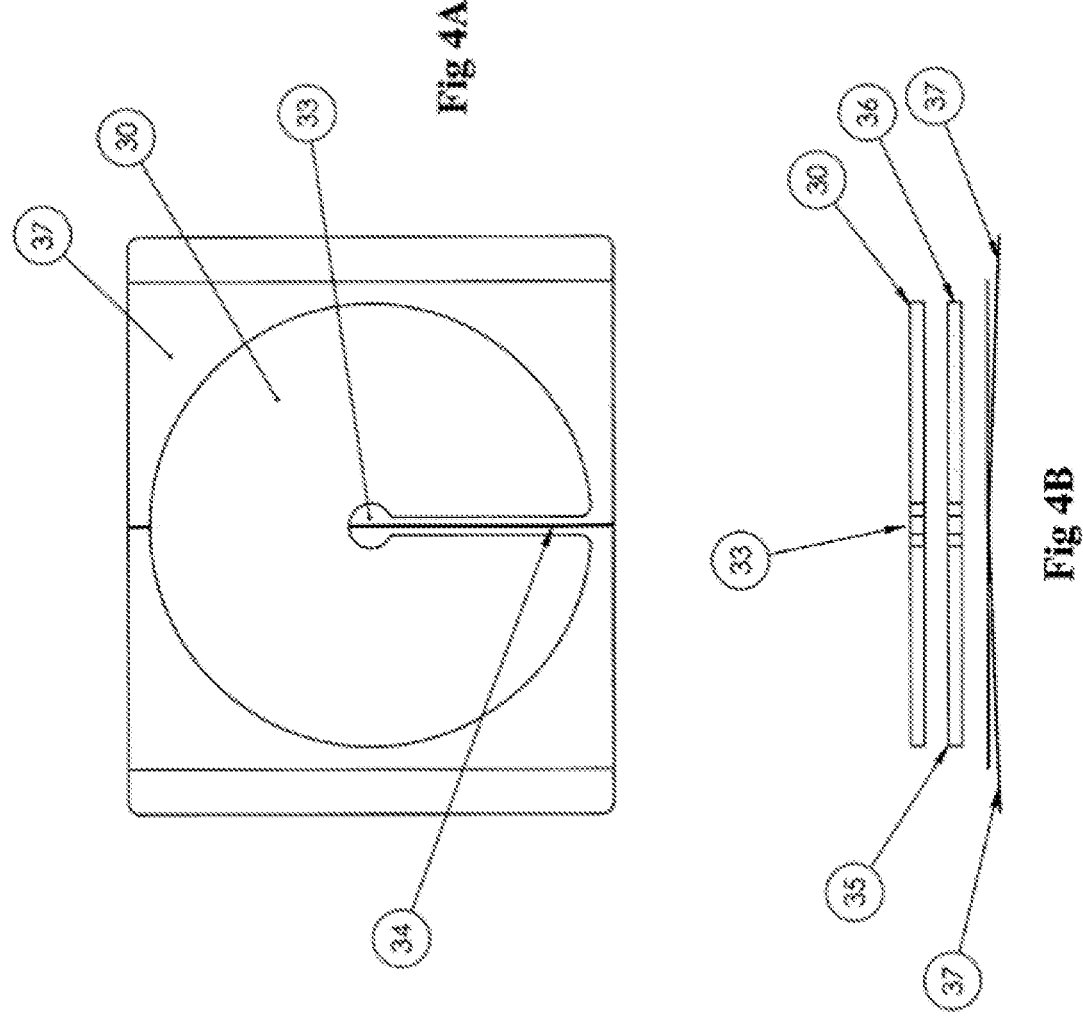
FIG. 4A is a top view of another embodiment of the invention.
FIG. 4B is a side view of the embodiment in FIG. 4A.

Referring now to FIG. 4A, a top view of another embodiment of the present invention is shown. A gas and water vapor transparent film 30 is shown. The bottom side of the film 30 is preferably coated with two types of acrylic adhesive, the adhesives are preferably separated along the radius cutout 33. Preferably, the transparent film 30 has a circular shape with an opening 33 placed in the center of the circle. A radius cutout 34 preferably provides a passage between the center cutout 33 and the perimeter of the transparent film 30. The transparent film 30 is preferably placed over two pieces of double folded release paper 37, with two internal edges of a release paper folds, being aligned with the radius cutout 34 for easy placement of the invention around a catheter insertion site (not shown).

Referring now to FIG. 4B, a side view of the embodiment shown in FIG. 4A is shown. As discussed above, the transparent film 30 is preferably covered with two types of adhesive. Side 35 shown in FIG. 4B is coated with an adhesive mixed with an antimicrobial agent. Side 36 shown in FIG. 4B is coated with an adhesive mixed with an antimicrobial agent and microencapsulated globs of TLC. This embodiment provides for a delivery of antimicrobial agent 360 degrees around the insertion site and 180 degrees temperature change visualization around the insertion site.

Figures 5A, 5B:
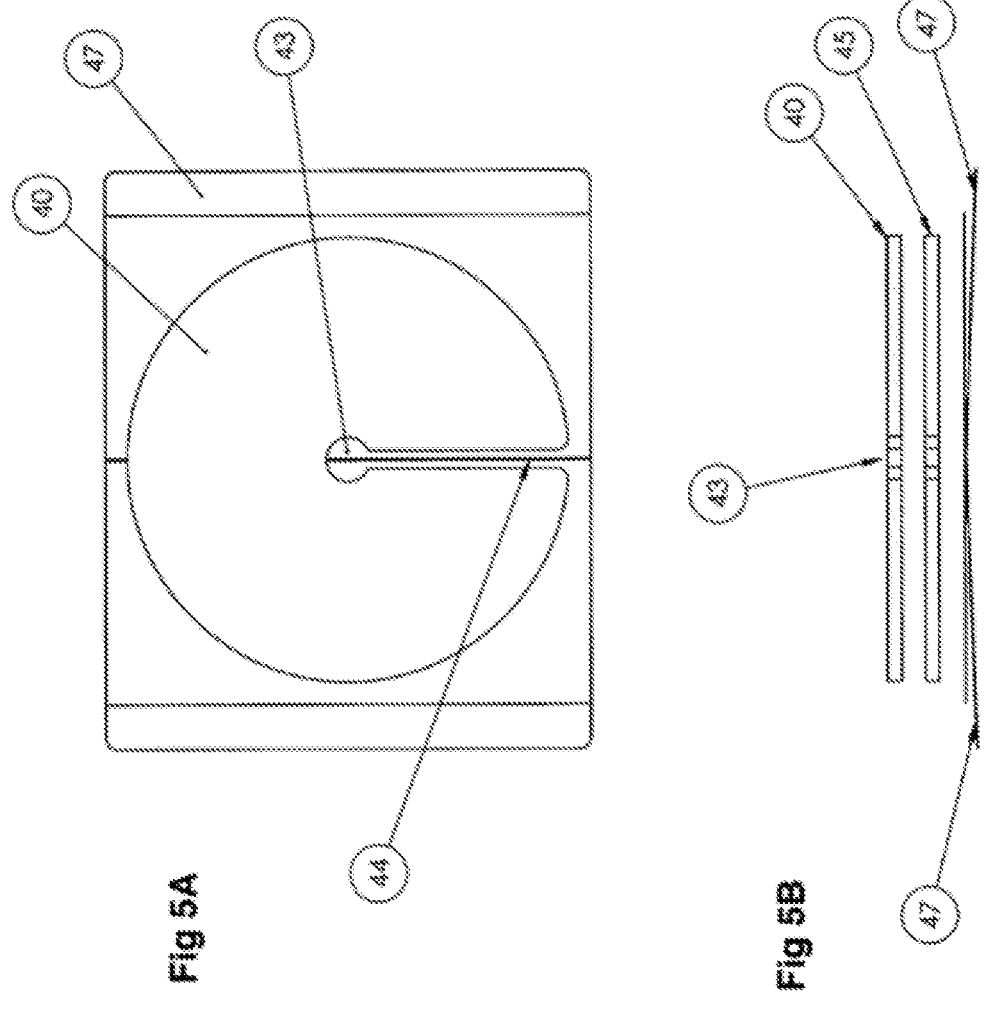
FIG. 5A is a top view of another embodiment of the invention.
FIG. 5B is a side view of the embodiment in FIG. 5A.

Referring now to FIG. 5A, a top view of another embodiment of the present invention is shown. In this embodiment, a transparent film or a copolymer cast 40 contains TLC as a dispersed aggregate. A change in color of the transparent film or cast 40 provides for the observation of temperature changes over the entire transparent film/cast areas. The transparent film or cast 40 has its bottom surface covered with an acrylic adhesive impregnated or mixed with an antimicrobial agent. Preferably, the transparent film/cast 40 has a circular shape with an opening 43, placed in the center of the circle. A radius cut out 44 preferably provides a passage between the center cutout 43 and the perimeter of the transparent film 40. The transparent film 40 is preferably placed over two pieces of double folded release paper 47, with two internal edges of a release paper folds, being aligned with the radius cutout 44, for easy placement of the invention around a catheter insertion site (not shown). Because the discrete aggregates of TLC, which are dispersed through the transparent film/cast 40, are also mixed with a black powder, a visual observation of the insertion site is limited.

Referring now to FIG. 5B, a side view of the embodiment shown in FIG. 5A, is shown. As discussed above, the transparent film/cast 40 is preferably covered on its patient side with an antimicrobial adhesive 45 and placed over the two parts of a double folded release paper 47.

Figures 6A, 6B:
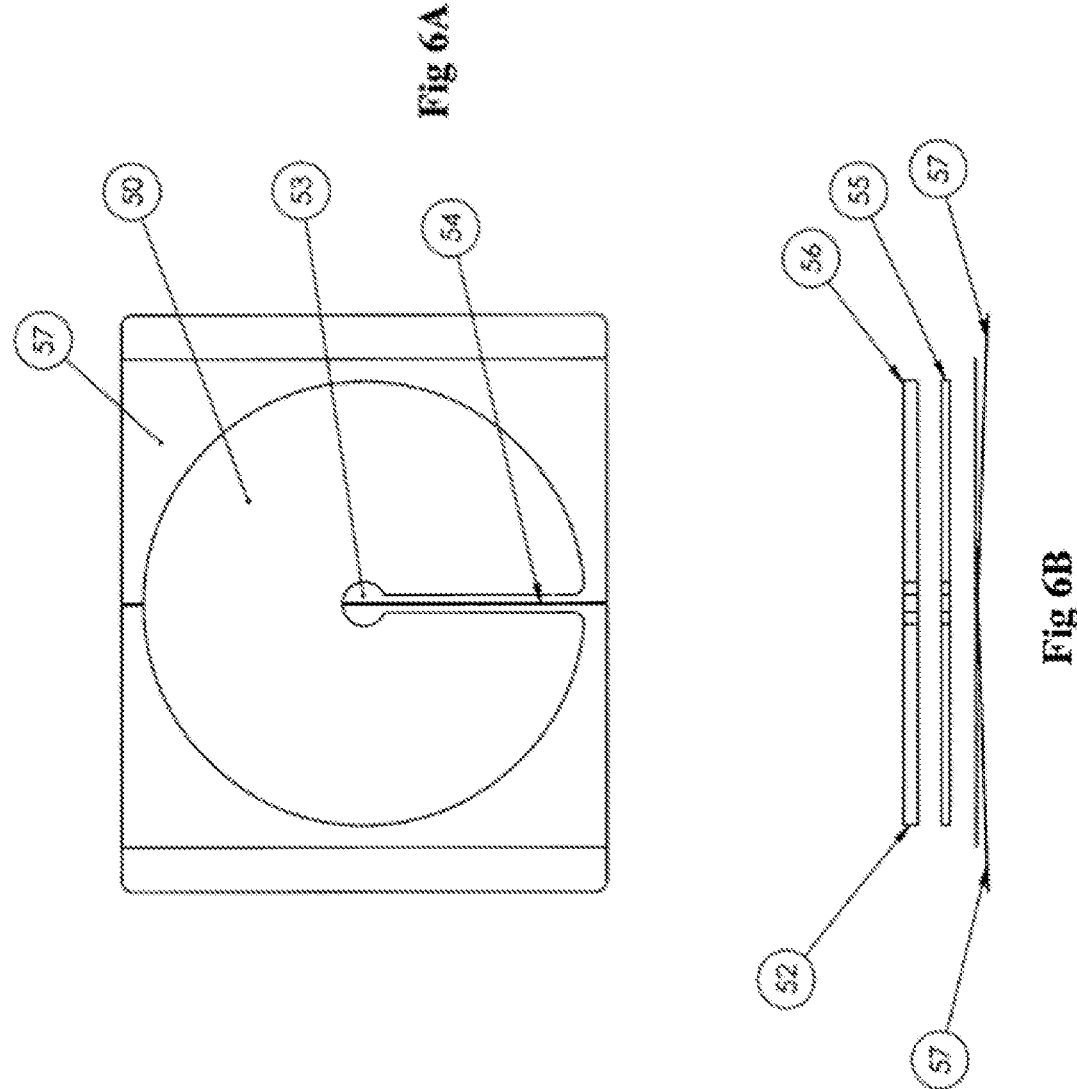
FIG. 6A is a top view of another embodiment of the invention.
FIG. 6B is a side view of the embodiment in FIG. 6A.

Referring now to FIG. 6A, a top view of another embodiment of the present invention is shown. A gas and water vapor transparent film/cast 50 is subdivided into two parts, which are separated along the radius cutout 54. The bottom side 55 of the film/cast 50 is coated with an acrylic adhesive impregnated/mixed with an antimicrobial agent. Preferably, the transparent film 50 has a circular shape with an opening 53 placed in the center of the circle. A radius cutout 54 preferably provides a passage between the center of the cutout 53 and the perimeter of the transparent fil/cast 50. The transparent film/cast 50 is preferably placed over the two pieces of double folded release paper 57 with 2 internal edges of a release paper folds being aligned with radius cutout 54 for easy placement of the invention around a catheter insertion site (not shown).

Referring now to FIG. 6B, a side view of the embodiment shown in FIG. 6A is shown. As discussed above, the transparent film/cast 50 is preferable subdivided into two sides. Side 52 is preferably transparent film/cast alone. Side 56 is preferably transparent film/cast with microencapsulated globes of TLC. This embodiment provide for a delivery of antimicrobial agent 360 degrees around the insertion site and provides for 180 degrees of temperature change visualization around the insertion site, and 180 degrees of visualization of the catheter insertion site.

Figures 7A, 7B:
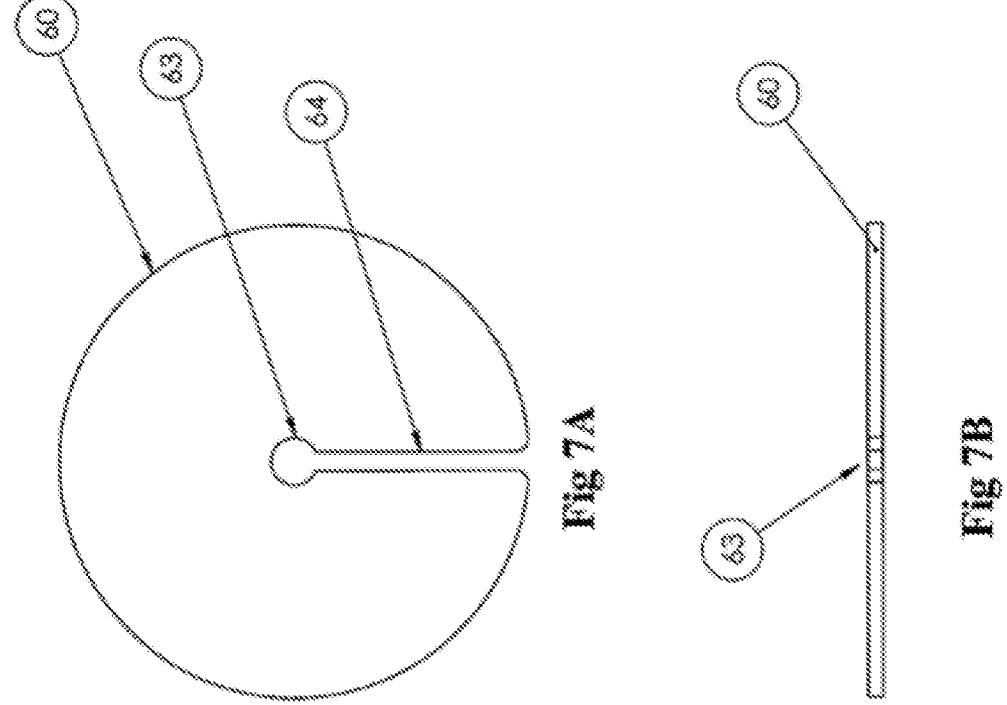
FIG. 7A is a top view of another embodiment of the invention.
FIG. 7B is a side view of the embodiment in FIG. 7A.

Referring now to FIG. 7A, a top view of another embodiment of the present invention is shown. In this embodiment a preferably non-transparent foam 60 without adhesive is formulated with a mixture of an antimicrobial agent and TLC or TLC alone, with antimicrobial agent being impregnated into the foam. There is a radius cutout 64 for sliding the foam around a catheter to place the catheter in the center cutout 63. The TLC allows the foam 60 to change color as an indicator of temperature changes. This color change is preferably observed over the entire surface of the circular foam 60. FIG. 7B, is a side view of this embodiment.

Referring now to FIGS. 8A and 8B, another embodiment of the present invention is shown. In this embodiment, a plurality of liquid crystal temperature sensitive films 71, preferably in the shape of a circle, are placed randomly or in a pattern over the surface of a gas and water vapor permeable transparent film 70. The transparent film 70 preferably has a smooth top surface and the bottom surface is coated with an acrylic adhesive impregnated with an antimicrobial agent 72. The TLC film 71 preferably has a smooth top surface and a bottom surface covered with an acrylic adhesive 73 to attach to the film 70. The transparent film 70 with its bottom surface adhesive 72 is attached to a release liner 77. A side view of the embodiment in FIG. 8A is shown in FIG. 8B.

Figures 9A, 9B:
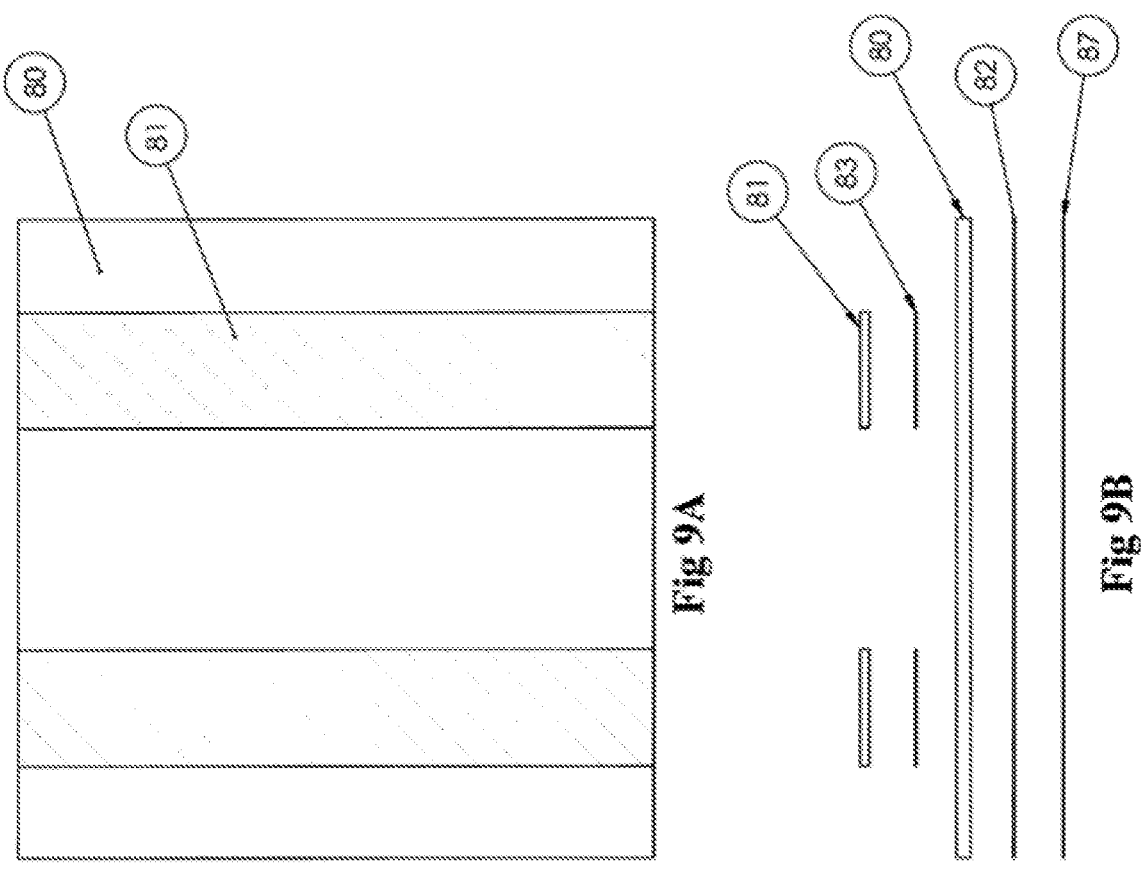
FIG. 9A is a top view of another embodiment of the invention.
FIG. 9B is a side view of the embodiment in FIG. 9A.

Referring now to FIG. 9A, a top view of another preferred embodiment of the invention is shown. In this embodiment, a liquid crystal temperature sensitive film TLC 81 is placed longitudinally or transversely on a gas and water vapor permeable transparent film 80. The transparent film 80 preferably has a smooth top surface and the bottom surface is coated with an acrylic adhesive impregnated with an antimicrobial agent 82. The liquid crystal temperature film 81 preferably has a smooth top surface and a bottom surface covered with an acrylic adhesive 83 to attach to the film 80. The adhesive 82 is covered with a release paper 87. A side view of the embodiment in FIG. 9A is shown in FIG. 9B.

Alternative Embodiments

Figures 10A, 10B:
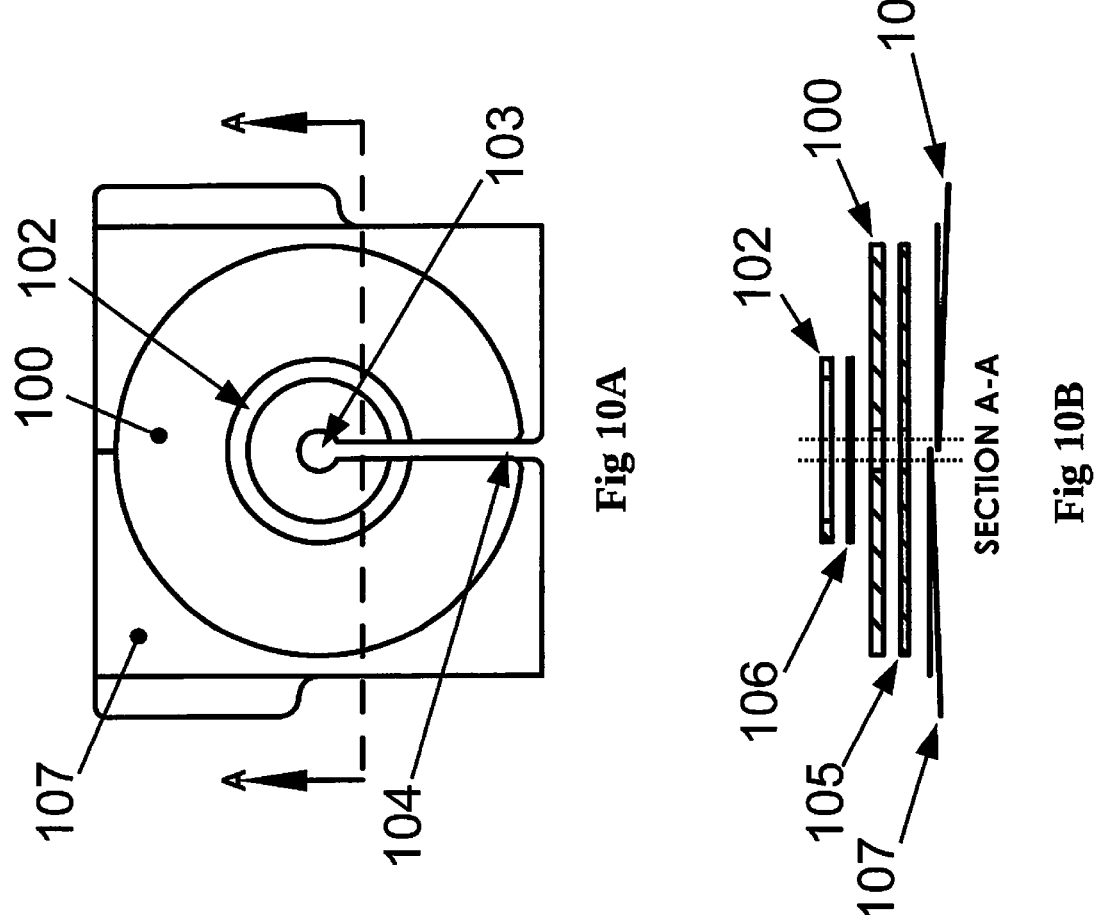
FIG. 10A is a top view of an alternative embodiment of the invention.
FIG. 10B is a side view of the embodiment in FIG. 10A.

Alternative embodiments for an improved integrated wound dressing device are shown and described in FIGS. 10A through 20B, inclusive. Referring now to FIG. 10A, a top view of the invention is shown. A gas and water vapor permeable transparent film 100 is shown. The bottom side of the film 100 is preferably coated with an acrylic adhesive impregnated with/permeated by an antimicrobial agent 105. A common example of such a film with antimicrobial adhesive is Bene Hold™ CHG transparent dressing. The bottom side is also referred to as the "patient side" because it contacts the patient's skin. The top side of the transparent film 100 is preferably smooth and faces away from the patient. Preferably, the transparent film 100 has a circular shape with an opening/collar 103 placed in the center of the circle or along the radial axis. As shown, a liquid crystal temperature sensitive film 102 with an adhesive, such as Edmund Optics™ liquid crystal sheet, having a 35-40° C. range, is placed centrally around the opening/collar 103 on the top side of the transparent film 100, with the collar opening 103 being larger than the sliding opening 104. A radius cutout/sliding opening 104 preferably provides a passage between the center cutout/collar 103 and the perimeter of the transparent film 100. The transparent film 100 is preferably placed over two pieces of double folded released paper 107. A release paper 107 has a radial slit and collar opening conforming to a radial slit and collar opening of a circular pad for easy placement of the invention around a catheter insertion site (not shown). In application, the radius cutout 104 is slid along the side of the catheter (not shown), until the catheter extends through the center cutout/collar 103. The wings of double folded release paper 107 are then pulled off to expose the adhesive/anti-microbial agent 105 on the bottom side so that the invention can be secured to the skin of the patient.

Referring now to FIG. 10B, a side view of the embodiment shown in FIG. 10A is shown. As discussed above, the transparent film 100 is preferably covered with an antimicrobial adhesive 105 and placed over the two parts of a double folded release paper 107. The liquid crystal temperature sensitive film 102 with adhesive 106 on its bottom surface is placed on the top surface of the transparent film 1. The liquid crystal film 102, preferably in the form of a ring, is placed concentrically around center cutout/collar 103. In this configuration, the changes in temperature are observed approximately 360 degrees (360 degrees minus the sliding opening 104) around a catheter insertion site and in proximity to the insertion site. Preferably, there is space between the inner circumference of the liquid crystal film 102 and the central opening/collar 103 and, thus, the outer circumference of the catheter (not shown) for visual observation of the catheter insertion site.

Figure 11A:
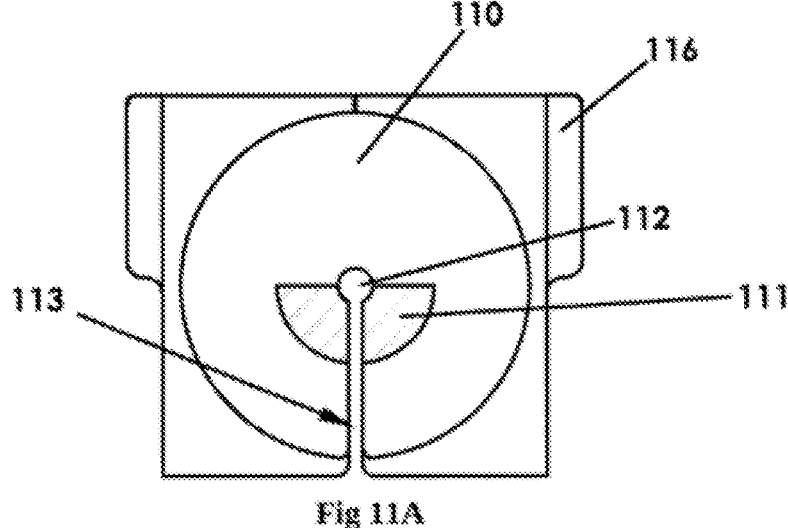
FIG. 11A is a top view of another alternative embodiment of the invention.

Referring now to FIG. 11A, a top view of another embodiment of the present invention is shown. A gas and water vapor permeable transparent film 110 is shown. The bottom side of the film 110 is preferably coated with an acrylic adhesive impregnated with/permeated by an antimicrobial agent 114. See FIG. 11B. The top side of the transparent film 110 is preferably smooth and faces away from the patient. Preferably, the transparent film 110 has a circular shape with a radial slit/sliding opening 113 and circular opening/collar 112 placed in the center of the circular pad, or at any point along the radial longitudinal axis. As shown, a liquid crystal temperature sensitive film 111 with an adhesive 115, in form of one half of a circle, is placed concentrically halfway around the opening 112 on the top side of the transparent film 110. The liquid crystal film 111 is cut in a shape to align with the one half of the opening/collar 112 and the opening/sliding area 113. The radial slits for each component of this embodiment are aligned. A radius cutout 113 preferably provides a passage between the center cutout/collar 112 and the perimeter of the transparent film 110. The transparent film 110 is preferably placed over two pieces of double folded released paper 116 for easy placement of the invention around a catheter insertion site (not shown).

Figure 11B:
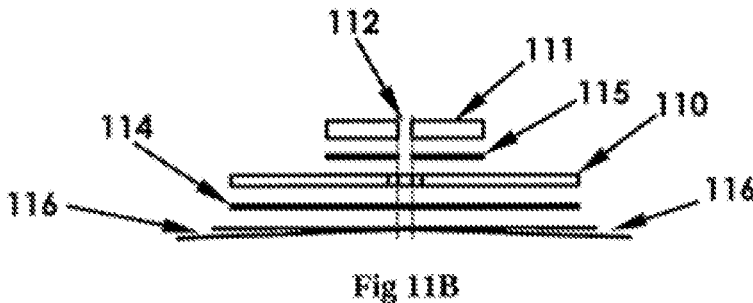
FIG. 11B is a side view of the embodiment in FIG. 11A.

Referring now to FIG. 11B, a side view of the embodiment shown in FIG. 11A is shown. As discussed above, the transparent film 110 is preferably covered with an antimicrobial adhesive 114 and placed over the two parts of a double folded release paper 116. The liquid crystal temperature sensitive film 111 with adhesive 115 on its bottom surface is placed on the top surface of the transparent film 110. The liquid crystal film 111, preferably in the form of a half circle, is placed around center cutout/collar 112. In this configuration, the changes in temperature are observed approximately 180 degrees around the catheter insertion site while the other 180 degrees provides for visible observation of the insertion site.

Figure 12A:
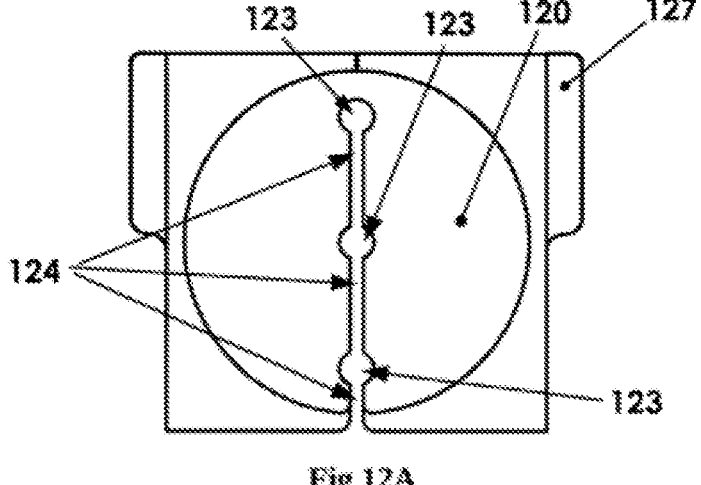
FIG. 12A is a top view of another alternative embodiment of the invention.

Referring now to FIG. 12A, a top view of another embodiment of the present invention is shown. In this embodiment, a transparent film 120 has its bottom surface covered with an acrylic adhesive impregnated or mixed with an antimicrobial agent and a non-toxic mixture of liquid crystal esters 125 (see FIG. 12B), providing for observation of temperature changes by observing the changes in color over the entire transparent film area. Preferably, the transparent film 120 has a circular shape with multiple openings/collars 123 placed on several points along the axis of the diameter, with cutouts/sliding area 124 for easy sliding of the circular pad over the catheter (not shown) to the appropriate circular opening/collar which depends on the space available around the catheter. The circular openings/collars 123 are interconnected with the cutout/sliding area 124. A diameter cutout 124 preferably provides a passage between the cutouts 123 and the perimeter of the transparent film 120. A release paper 127 has a radial slit aligned with the diameter cutout 124 and also conforming to a radial slit of a circular pad for easy placement of the invention around a catheter insertion site (not shown). A visual observation of the insertion site is limited with this embodiment because microencapsulated globes of TLC, which are dispersed through the acrylic adhesive, are preferably coated with the carrier mixed with black powder.

Figure 12B:
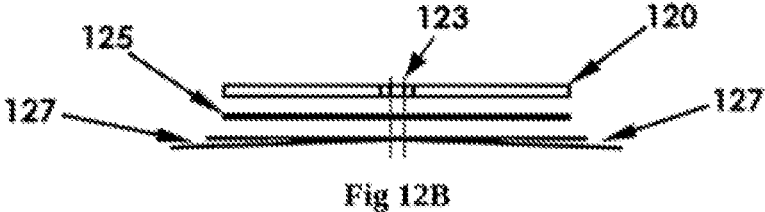
FIG. 12B is a side view of the embodiment in FIG. 12A.

Referring now to FIG. 12B, a side view of the embodiment shown in FIG. 12A is shown. As discussed above, the transparent film 120 is preferably covered with an antimicrobial adhesive 125 mixed with microencapsulated globes of TLC 125 and placed over the two parts of a double folded release paper 127.

Figure 13A:
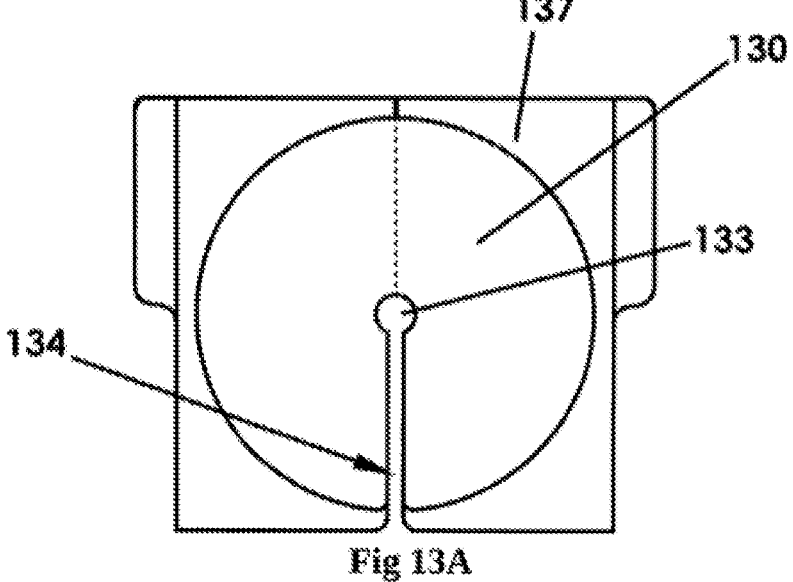
FIG. 13A is a top view of another alternative embodiment of the invention.

Referring now to FIG. 13A, a top view of another embodiment of the present invention is shown. A gas and water vapor permeable transparent film 130 is shown. The bottom side of the film 130 is preferably coated with two types of acrylic adhesive, the adhesives are preferably separated along the diameter cutout 134. Preferably, the transparent film 130 has a circular shape with an opening/collar 133 placed in the center of the circular pad. Diameter cutout/sliding area 134 preferably provides a passage between the center cutout/collar 133 and the perimeter of the transparent film 130. The transparent film 130 is preferably placed over two pieces of double folded release paper 137, the release paper has a radial slit aligned to a radial slit of the circular pad, for easy placement of the invention around a catheter insertion site (not shown).

Figure 13B:
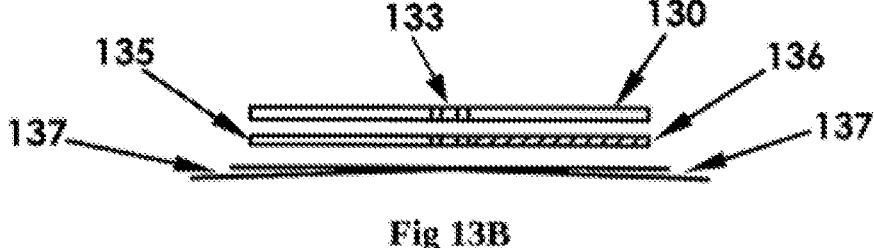
FIG. 13B is a side view of the embodiment in FIG. 13A.

Referring now to FIG. 13B, a side view of the embodiment shown in FIG. 13A is shown. As discussed above, the transparent film 130 is preferably covered with two types of adhesive. A first side 135 of film 130 is coated with an adhesive mixed with an antimicrobial agent. A second side 136 is coated with an adhesive mixed with an antimicrobial agent and microencapsulated globes of TLC. This embodiment provides for a delivery of antimicrobial agent approximately 360 degrees around the insertion site and 180 degrees temperature change visualization around the insertion site.

Figure 14A:
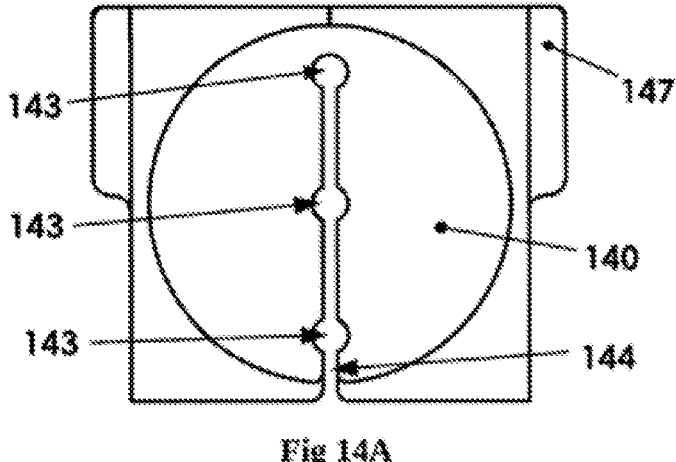
FIG. 14A is a top view of another alternative embodiment of the invention.

Referring now to FIG. 14A, a top view of another embodiment of the present invention is shown. In this embodiment, a transparent film or a copolymer cast 140 contains TLC as a dispersed aggregate. A change in color of the transparent film or cast 140 provides for the observation of temperature changes over the entire transparent film/cast areas. The transparent film or cast 140 has its bottom surface covered with an acrylic adhesive impregnated or mixed with an antimicrobial agent 145. Preferably, the transparent film/cast 140 has a circular shape with openings/collars 143 placed along a diameter axis of the embodiment. A diameter cut out 144 preferably provides a passage between the cutouts/collars 143 and the perimeter of the transparent film 140. The transparent film 140 is preferably placed over two pieces of double folded release paper 147, the release paper 147 preferably has a diameter slit with collars aligned with diameter cut out 144 and collars 143 above for easy placement of the invention around a catheter insertion site (not shown). Because the discrete aggregates of TLC, which are dispersed through the transparent film/cast 140, are also mixed with a black powder, a visual observation of the insertion site is limited.

Figure 14B:
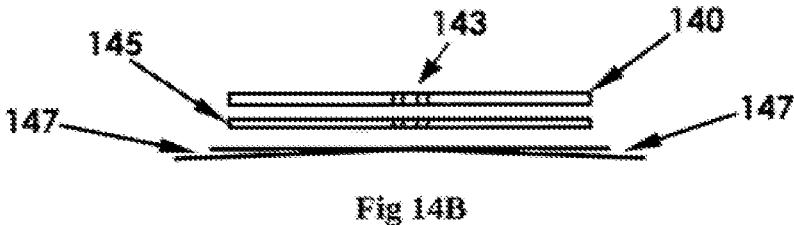
FIG. 14B is a side view of the embodiment in FIG. 14A.

Referring now to FIG. 14B, a side view of the embodiment shown in FIG. 14A, is shown. As discussed above, the transparent film/cast 140 is preferably covered on its patient side with an antimicrobial adhesive 145 and placed over the double folded release paper 147.

Figure 15A:
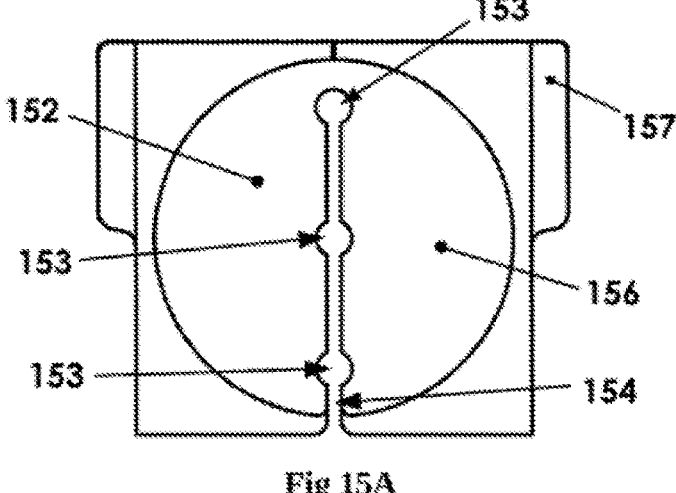
FIG. 15A is a top view of another alternative embodiment of the invention.

Referring now to FIG. 15A, a top view of another embodiment of the present invention is shown. A gas and water vapor permeable transparent film/cast is subdivided into two parts 152 and 156 respectively, which are separated along the diameter slit/cutout 154. The bottom side 155 of the film/cast 152 and 156 is coated with an acrylic adhesive impregnated/mixed with an antimicrobial agent. Preferably, the transparent film 152/156 has a circular shape with openings 153 placed along a diameter axis. A diameter slit/cutout 154 preferably provides a passage between the cutout/collars 153 and the perimeter of the transparent film/cast 152 and 156. The transparent film/cast is preferably placed over the two pieces of double folded release paper 157 with two (2) internal edges of a release paper folds being aligned with diameter slit/cutout 154. The release paper 157 preferably has a diameter slit aligned to diameter slit/cutout 154, for easy placement of the invention around a catheter insertion site (not shown)

Figure 15B:
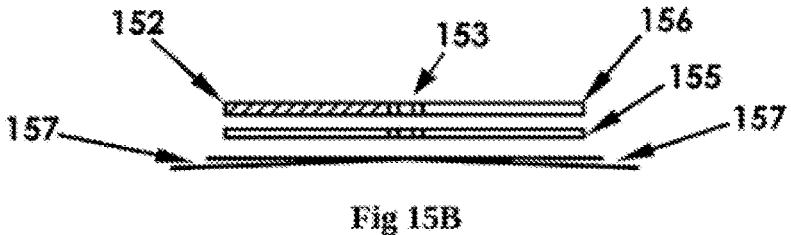
FIG. 15B is a side view of the embodiment in FIG. 15A.

Referring now to FIG. 15B, a side view of the embodiment shown in FIG. 15A is shown. As discussed above, the transparent film/cast is preferable subdivided into two sides, 152 and 156. Both sides are coated with an adhesive with an antimicrobial agent, but the second side 156 is preferably transparent film/cast antimicrobial agent with microencapsulated globes of TLC. This embodiment provides for a delivery of antimicrobial agent approximately 360 degrees around the insertion site and provides for 180 degrees of temperature change visualization around the insertion site.

Figure 16A:
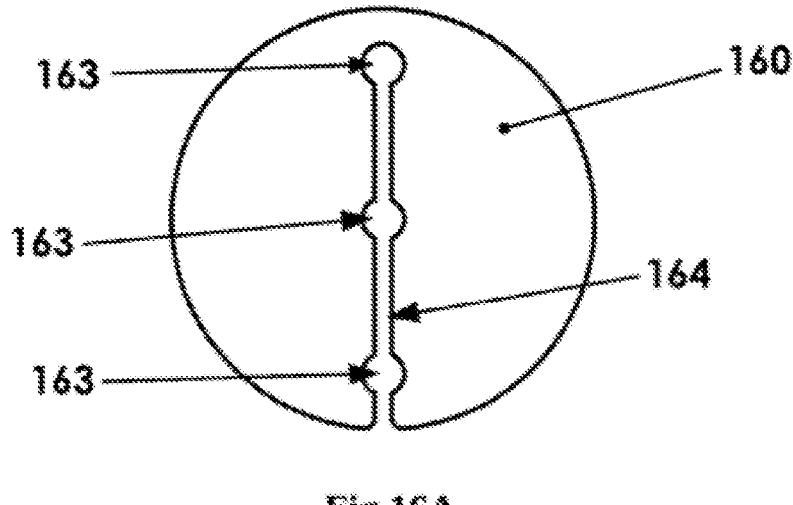
FIG. 16A is a top view of an alternative embodiment of the invention.
Figure 16B:
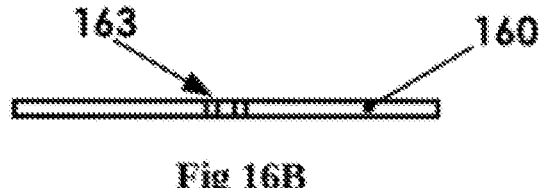
FIG. 16B is a side view of the embodiment in FIG. 16A.

Referring now to FIG. 16A, a top view of another embodiment of the present invention is shown. In this embodiment, a preferably non-transparent foam 160 without adhesive is formulated with a mixture of an antimicrobial agent and TLC or TLC alone. If an antimicrobial agent is present, it is preferably impregnated into the foam. The embodiment preferably comprises a diameter cutout 164 for sliding the foam 160 around a catheter (not shown) to place the catheter in one of the multiple circular openings/collars 163, along a diameter axis. The TLC allows the foam 160 to change color as an indicator of temperature changes. This color change is preferably observed over the entire surface of the circular foam 160. Referring now to FIG. 16B, a side view of the embodiment in FIG. 16A is shown.

Figures 17A, 17B:
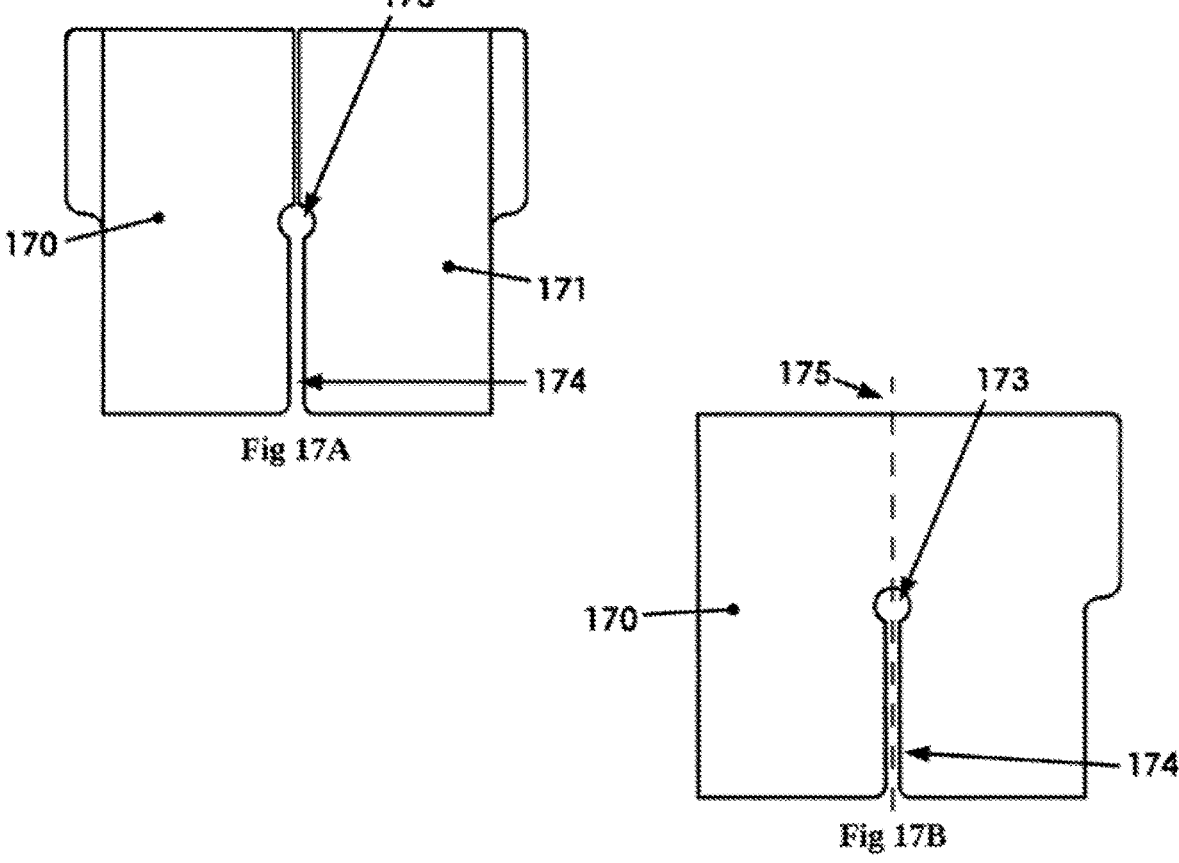
FIG. 17A is a top view of an alternative embodiment of release liner.
FIG. 17B is a side view of the release liner in FIG. 17A.

Referring now to FIG. 17A, a top view of left release paper 170 and right release paper 171 are shown attached to the adhesive of the bottom/patient side of the circular pad. The release papers 170, 171 preferably have a circular opening/collar 173 and a radial cutout 174. In application, each release paper is folded centrally along its radial or diameter axis forming a communication path between the collar's circumference and the paper's perimeter. When folded release papers are placed on the patient side of circular pad, they must conform with circular pad collars and cutouts. Referring now to FIG. 17B, a top view of the right side of 171, the release liner in unfolded position is shown. When placed over the right side of the circular pad, the release liner 171 is folded along its radial axes 175.

Figure 18A:
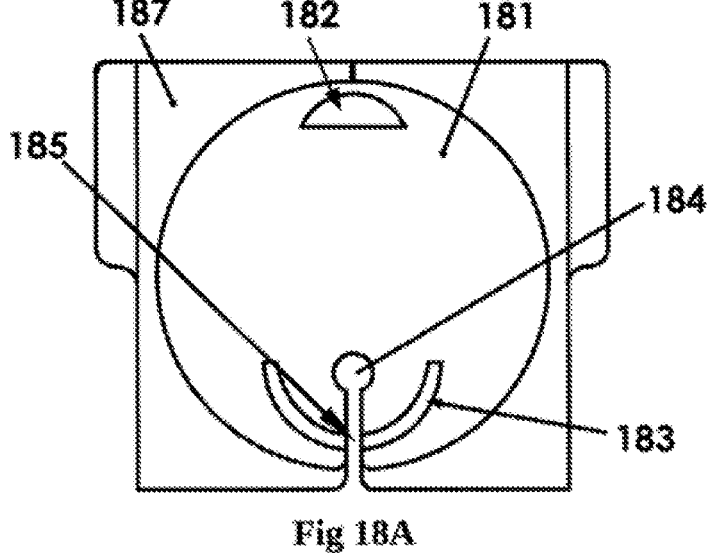
FIG. 18A is a top view of another alternative embodiment of the invention.
Figure 18B:
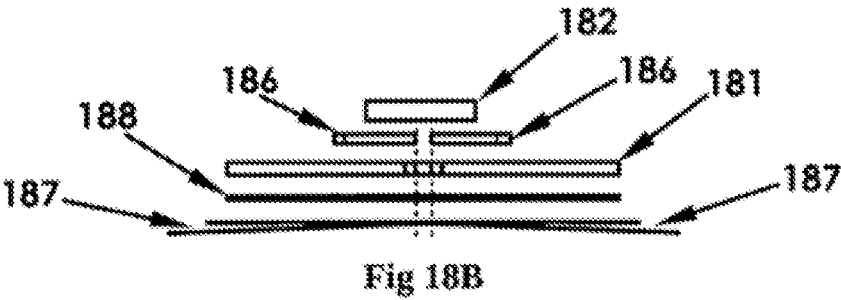
FIG. 18B is a side view of the embodiment in FIG. 18A.

Referring now to FIGS. 18A and 18B, a top and side view of another embodiment of the present invention is shown. A circular pad 181 has a top surface and a bottom (or patient-contact) surface. The bottom/patient contact surface is preferably covered with adhesive containing antimicrobial agents 188. The smooth top surface preferably has temperature sensitive components comprising a quarter circle 182, placed on the diameter axis close to the perimeter of the circular pad 181, and a half ring 183 with a transverse diameter aligned with collar 184. Collar 184 and radial opening 185 are placed on a radial axis between the center and the perimeter of the circular pad 181, cutting the temperature sensitive ring to two (2) segments. The circular pad 181 is preferably placed over two (2) pieces of double folded release paper 187. The release paper 187 preferably has a radial slit conforming to the radial slit 185 of circular pad 181. In this configuration, patient temperature can be measured at two (2) locations, 182 and 183. The temperature component 183 in proximity of the collar 184 measures the insertion site temperature, the temperature component 182 on the perimeter of the circle 181 measures normal skin temperature.

Figure 19A:
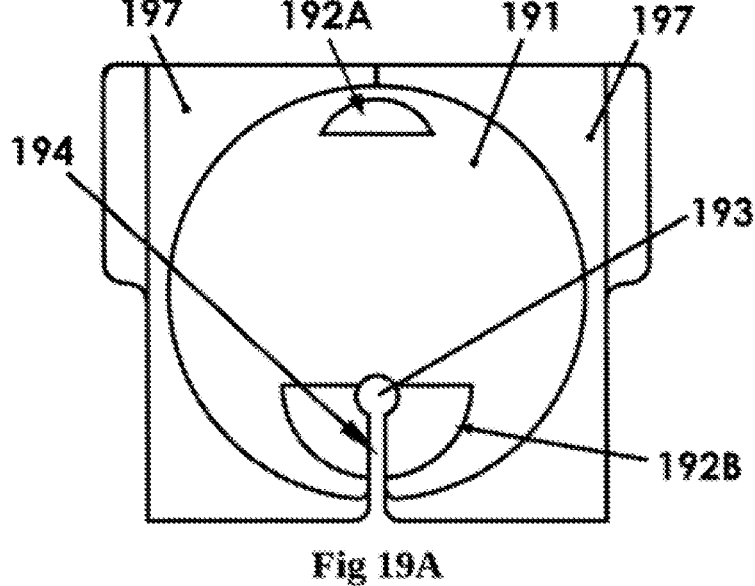
FIG. 19A is a top view of another alternative embodiment of the invention.
Figure 19B:
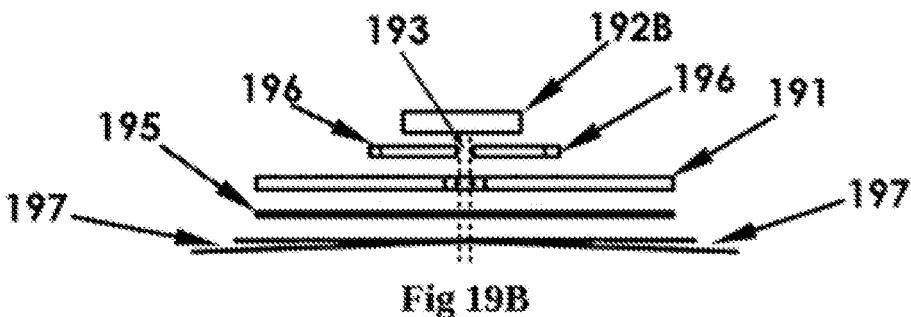
FIG. 19B is a side view of the embodiment in FIG. 19A.

Referring now to FIGS. 19A and 19B, a top and side view of another embodiment of the present invention are shown, respectively. A circular pad 191 is shown with its top surface and bottom surface. A bottom/patient contacting surface of pad 191 is preferably covered with adhesive containing antimicrobial agents 195. The smooth top surface of pad 191 preferably has two temperature sensitive components, a quarter circle 192A, preferably placed on a diameter axis close to the perimeter of the circular pad 191, and the other preferably in the form a half circle 192B, preferably with the transverse diameter being aligned with the lower half of collar 193. Collar 193 and radial opening 194 are preferably placed on a radial axis of pad 191 between the center and the perimeter of circular pad 191, cutting the temperature sensitive circle 194 into two (2) segments. The circular pad 191 is preferably placed over two (2) pieces of double folded release paper 197. The release paper 197 preferably has a radial slit aligned with radial slit 193 of the circular pad 191. In this configuration, temperature can be measured at two locations 192A and 192B. The catheter insertion site temperature is preferably measured by the temperature component 192B in the proximity of the collar 193. The temperature component 192A on the perimeter of the circle 191 preferably measures normal skin temperature.

Figure 20A:
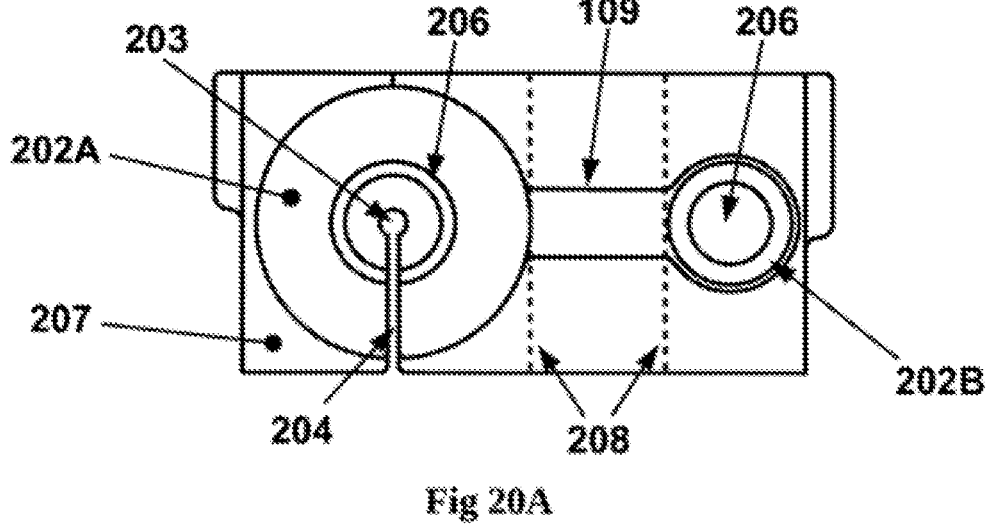
FIG. 20A is a top view of another alternative embodiment of the invention; and, FIG. 20B is a side view of the embodiment in FIG. 20A.
Figure 20B:
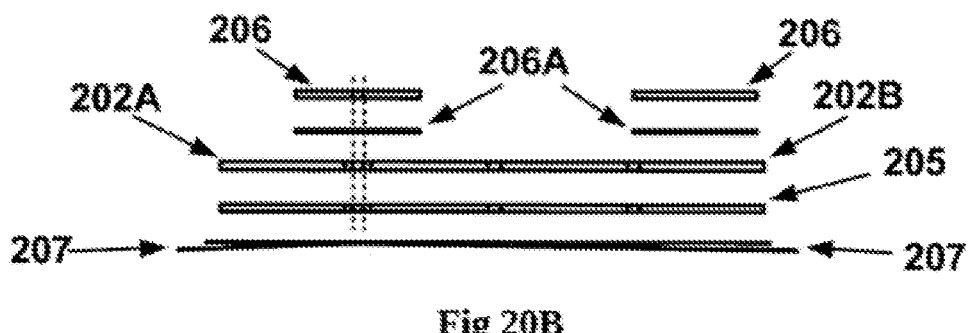

Referring now to FIGS. 20A and 20B, a top and side view of another embodiment of the present invention is shown. A circular pad 202A is shown having a side arm 209 preferably extending radially from perimeter of the circular pad 202A. The circular pad 202A preferably has a top and bottom surface, with the bottom surface/patient contacting surface being covered with an adhesive containing antimicrobial agents 205. The smooth top surface preferably has temperature sensitive components 206, one of said components 206 preferably in the form of a ring concentrically placed around a center cutout/collar 203. Collar 203 and radial opening 204 are preferably placed on a radial axis of circular pad 202A. Preferably, the collar 203 is placed in the center of the circular pad 202A. The side arm 209, preferably comprised of narrow strip of material, is shown connecting the first/large circular pad 202A with a second/small circular pad 202B, which on its top surface has a temperature sensitive component 206, preferably in the form of a circle. Both temperature sensitive compounds 206 are attached to the upper surface of first circular pad 202A and second circular pad 202B by an adhesive 206A. Both the arm 209 and the small circle 202B on their bottom side are coated with an adhesive containing antibacterial agents 205. Preferably, there are tangential perforations 208 at the arm 209 between the first/large 202A and second/small circle 202B. The circular pad 202A with the side arm 209 and small circle 202B is preferably placed over two pieces of double folded release paper 207. The release paper 207 preferably has a radial slit, conforming to the radial slit 204 of the circular pad 202A with one side of the release paper 207 preferably extending under the side arm 209 and second/small pad 202B. In this configuration, temperature can be measured at two locations. The temperature component 206, in proximity of the collar 203 of a first/large circular pad 202A, preferably measures catheter insertion site temperature. The temperature component 206 placed on the second/small circle 202B preferably measures normal skin temperature and can be placed anywhere on the body by separating second/small circular pad using perforations.

Thus, an improved integrated wound dressing device incorporating a single point or two points of differential temperature indications for early detection and treatment of an insertion site of percutaneous and drug delivery devices is described above. In each of the above embodiments, the different positions and structures of the present invention are described separately in each of the embodiments. However, it is the full intention of the inventor of the present invention that the separate aspects of each embodiment described herein may be combined with the other embodiments described herein. Those skilled in the art will appreciate that adaptations and modifications of the just-described preferred embodiment can be configured without departing from the scope and spirit of the invention. Therefore, it is to be understood that, within the scope of the appended claims, the invention may be practiced other than as specifically described herein.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. Likewise, the various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An integrated catheter insertion site dressing device comprising:
   a large circular pad and a small circular pad interconnected by a side arm;
   the large circular pad having a perimeter and a diameter, a top surface and a bottom patient contact surface, a slit extending up to 80% of the diameter to the perimeter of the circular pad, the slit further comprising one or more circular collars;
   the small circular pad having a small pad perimeter, a small pad top surface and a small pad bottom patient contact surface;
   a release liner with a release liner slit and one or more release liner collars; and,
   antimicrobial and temperature indicator components on the large circular pad and the small circular pad for differential temperature indication.

2. The integrated catheter insertion site dressing device of claim 1, where the large circular pad comprises of a transparent area and a non-transparent area.

3. The integrated catheter insertion site dressing device of claim 2 where the non-transparent area comprises a shape selected from the group consisting of: a full circular pad, a half of a circular pad, a coaxial ring, and a half of a coaxial ring.

4. The integrated catheter insertion site dressing device of claim 2 where the release liner is double folded release paper having an upper surface attached to the bottom patient contact surface of the circular pad; where the release liner has a diameter and a release liner slit with one or more release liner collars, the release liner slit and one or more release liner collars conforming to the slit and one or more collars of the large circular pad, and where the upper surface, above the one or more release liner collars, provides a liner's fold.

5. The integrated catheter insertion site dressing device of claim 1, where the large circular pad is for insertion site temperature indication and is removable from the side arm at a first perforation and the small circular pad is removable from the side arm at a second perforation.

6. The integrated catheter insertion site dressing device of claim 1, where the antimicrobial and temperature indicator components are present in a film, cast or adhesive.

* * * * *